United States Patent [19]

Ruwart et al.

[11] Patent Number: 5,124,158
[45] Date of Patent: Jun. 23, 1992

[54] TRANSDERMAL ANTISECRETORY AGENTS FOR GASTROINTESTINAL DISEASE

[75] Inventors: Mary J. Ruwart, Kalamazoo; Wha B. Im, Portage, both of Mich.

[73] Assignee: The Upjohn Company, Kalamazoo, Mich.

[21] Appl. No.: 623,884

[22] PCT Filed: May 1, 1989

[86] PCT No.: PCT/US89/01757
§ 371 Date: Dec. 20, 1990
§ 102(e) Date: Dec. 20, 1990

[51] Int. Cl.$^5$ .............................................. A61F 13/00
[52] U.S. Cl. ..................... 424/449; 424/447; 424/448; 546/271
[58] Field of Search ...................... 424/448, 449, 447; 546/271

[56] References Cited

U.S. PATENT DOCUMENTS

| 4,255,431 | 3/1981 | Junggren | 424/263 |
| 4,575,554 | 3/1986 | Sih | 546/271 |
| 4,743,588 | 5/1988 | Mirejovsky | 514/24 |
| 4,911,916 | 3/1990 | Cleary | 424/449 |
| 4,915,950 | 4/1990 | Miranda et al. | 424/447 |

FOREIGN PATENT DOCUMENTS 2191693 12/1987 United Kingdom .

Primary Examiner—Thurman K. Page
Assistant Examiner—Leon R. Horne
Attorney, Agent, or Firm—Donald Corneglio

[57] ABSTRACT

A method for the treatment of gastrointestinal disease through a transdermally administered antisecretory agent. Antisecretory agents useful for transdermal administration are substituted 2-pyridylmethylthio- and sulfinyl-benzimidazoles and omeprazole.

10 Claims, No Drawings

TRANSDERMAL ANTISECRETORY AGENTS FOR GASTROINTESTINAL DISEASE

CROSS-REFERENCE TO RELATED PATENT APPLICATIONS

This application is the national phase of international application PCT/US89/01757.

BACKGROUND OF THE INVENTION

The present invention is directed toward the treatment of gastrointestinal disease through a transdermally administered antisecretory agent. Antisecretory agents shown to be useful for transdermal administration are substituted 2-pyridylmethylthio- and sulfinyl-benzimidazoles and omeprazole.

One means for preventing or treating gastrointestinal diseases, specifically gastric and duodenal ulcers, is by the inhibition of gastric acid secretion. In situations where the integrity of the gastric mucosal barrier is compromised, gastric acid secretion can result in erosion of the epithelial cells with consequent inflammation and ulceration. Prevention and healing of such untoward gastric acid-induced effects can be achieved by the administration of a pharmacological agent which effectively inhibits gastric acid secretion.

Various effective agents are known such as substituted 2-pyridylmethylthio- and sulfinyl-benzimidazoles which are described in U.S. Pat. No. 4,575,554 and are herein incorporated by reference. Omeprazole is another compound known to be effective for the inhibition of gastric acid secretion which is described in U.S. Pat. No. 4,255,431 herein incorporated by reference.

Another important aspect to the prevention or treatment of gastrointestinal disease is the continuous, rather than intermittant, inhibition of gastric acid. It is therefore desirable to administer the drugs in a slow continuous fashion over a long period of time such that excess gastric acid secretion is minimized to prevent gastrointestinal disease. Another important consideration is ease of administration and comfort.

U.S. Pat. No. 4,575,554 discloses that a continuous inhibition of acid can be achieved by administering a single dose of these compounds subcutaneously. Until this time, subcutaneous administration of this class of compounds was the only choice when a long duration of action (several days or weeks) is desired with a single dose. Unfortunately, subcutaneous injection are not comfortable and sometimes can cause irritation to the surrounding tissue. Also, in the event of toxicity problems removal is difficult.

Transdermal administration of drugs such as by patches, gels, pastes, or other known vehicles is not only convenient but for the most part painless, simple to apply and easy to remove during adverse reactions. Unfortunately, many drugs can not be applied in this manner because they do not cross the skin readily enough to give the desired efficacy. Unexpectedly it has been discovered that the class of gastric anti-secretory drugs, substituted 2-pyridylmethylthio- and sulfinyl-benzimidazoles and omeprazoles, can be administered transdermally and still effectively inhibit the enzyme responsible for gastric acid secretion.

INFORMATION DISCLOSURE

U.S. Pat. No. 4,575,554 discloses the oral and parenteral administration of substituted 2-pyridylmethylthio- and sulfinyl-benzimidazoles for the treatment of gastrointestinal diseases.

U.S. Pat. No. 4,255,431 discloses a method and composition including omeprazole for inhibiting gastric acid secretion.

SUMMARY OF THE INVENTION

The present invention is directed toward a method and transdermal composition for inhibiting the secretion of gastric acid for prevention or treatment of gastrointestinal disease comprising the application to the skin of a mammal, including humans, a therapeutically effective amount of a compound of formula I

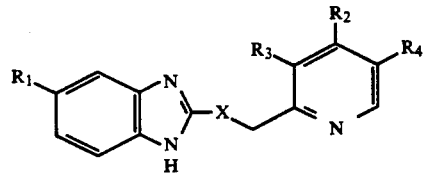

wherein
X is
  (a) =S, or
  (b) =S→O;
$R_1$ is
  (a) hydrogen,
  (b) methyl,
  (c) methoxy, or
  (d) trifluoromethyl;
$R_2$ is
  (a) methoxy, or
  (b) —$SR_5$ wherein $R_5$ is ($C_1$–$C_4$)alkyl, ($C_1$–$C_4$)alkenyl, PhX, —$CH_2$PhX, or ($C_3$–$C_{10}$)cycloalkyl, wherein "PhX" is phenyl substituted by zero to 3 of the following: ($C_1$–$C_4$)alkyl, chloro, fluoro, bromo, nitro, trifluoromethyl, or $OR_3$; and
$R_3$ and $R_4$ are the same or different and are
  (a) hydrogen, or
  (b) ($C_1$–$C_4$)alkyl.

Generally the compounds are first dissolved in a transdermal cream, paste, gel or liquid or otherwise absorbed into a transdermal patch. Preferred compounds derived from Formula 1 are 2-(4-ethylthio-3-methylpyridin-2-yl methyl)sulfinyl-benzimidazole and omeprazole. Omeprazole is where X is =S→O, $R_1$ and $R_2$ are methoxy and $R_3$ and $R_4$ are methyl.

The compound is dissolved in a transdermal vehicle in an amount of from about 1 to about 300 mg/dose. The dissolved compound can then be applied to the skin of a mammal, preferably a human being, to be absorbed through the skin such that the ($H^+$-$K^+$) ATPase enzyme responsible for gastric acid secretion is inhibited.

DETAILED DESCRIPTION OF THE INVENTION

The present invention relates to the effective transdermal administration of substituted 2-pyridylmethylthio- and sulfinyl-benzimidazoles, omeprazole or a pharmaceutically acceptable salt thereof for inhibition of gastric acid secretion. The gastric acid secretion is controlled by inhibiting gastric ($H^+$-$K^+$) ATPase activity.

The 2-pyridylmethylthio- and sulfinyl- benzimidazole compounds are described in U.S. Pat. No. 4,575,554 herein incorporated by reference. The omeprazole compound is described in U.S. Pat. No. 4,255,431 herein incorporated by reference. Generally these compounds are structurally represented by Formula I, shown above, wherein X is $=S$, or $=S\rightarrow O$; $R_1$ is hydrogen, methyl, methoxy, or trifluoromethyl; $R_2$ is methoxy or $-SR_5$ wherein $R_5$ is $(C_1-C_4)$alkyl, $(C_1-C_4)$alkenyl, PhX, $-CH_2PhX$ or $(C_3-C_{10})$ cycloalkyl, wherein "PhX" is phenyl substituted by zero to 3 of the following: $(C_1-C_4)$alkyl, chloro, fluoro, bromo, nitro, trifluoromethyl, or $OR_3$; and $R_3$ and $R_4$ are the same or different and are hydrogen, or $(C_1-C_4)$alkyl.

A preferred compound from this family is 2-(4-ethylthio-3-methylpyridin-2-yl methyl)sulfinyl-benzimidazole and omeprazole which is when X is $=S\rightarrow O$, $R_1$ and $R_2$ are methoxy and $R_3$ and $R_4$ are methyl.

The foregoing compounds are dissolved in a suitable transdermal vehicle such as a cream, gel, paste or liquid which are generally known in the art for transdermal use. Typical transdermal compounds are polyethylene glycol, propylene glycol, triacetin, propylcarbonate, ethanol and isopropyl myristate. The compounds can also be applied to porous or other material suitable for preparing a transdermal patch which can be worn by the patient. Such transdermal vehicles are generally well-known in the pharmaceutical industry and therefore will not be discussed in detail.

The compounds are transdermally applied in a therapeutically effective amount to inhibit gastric acid secretion. Generally the amount is from about 1 to about 300 mg/dosage, preferably about 100 to about 200 mg/dosage. However it is to be recognized that the amount used in the transdermal vehicle is greatly in excess of the amount actually transferred into the body. A typical cross-over rate is generally much less than the available drug present in the transdermal vehicle. The dosage is of course dependent upon the patient and diagnosed condition.

In order to prove the effectiveness of the transdermal administration, the subject compounds were dissolved in dimethyl sulfoxide (DMSO) and applied to the backs of rats and onto the ears of rabbits. The animals were allowed to rest for varying amounts of time and then the inhibition of $(H^+-K^+)$ ATPase, the enzyme responsible for gastric acid secretion, was measured. The results indicated that the compounds were absorbed such that $(H^+-K^+)$ ATPase was inhibited.

The following examples further describe and demonstrate the subject invention. For each of the following examples the drug dilutions were prepared in DMSO to a final concentration of 150 mg/ml. The drug was made fresh prior to each application.

The inhibition of $(H^+-K^+)$ ATPase activity was determined as described by Im, W. B.; Blalkeman, D. P., "Inhibitiion of Gastric $pH^+-K^+$) ATPase by Unsaturated Long Chain Fatty Acids" Biochem. et Biophy. Acta 692:355-60 (1982). For the rat models, fundic gastric mucosal microsomes were prepared and $(H^+-K^+)$ ATPase activity in the microsomes was estimated by measuring $K^+$-dependent ATP-hydrolysis.

For the rabbit models, mucosa from the fundic region was removed by blunt dissection and minced with scissors. 2.5 g of the minced tissue was placed in 25 ml of buffer containing 250 mM sucrose, 2 mM $MgCl_2$, 1 mM EGTA, and 2 mM Hepes/Tris, pH 7.4. The tissues were then prepared as described for the rat gastric mucosa.

EXAMPLE 1

Effect of Transdermal 2-(4-ethylthio-3-methylpyridin-2-yl methyl)sulfinyl-benzimidazole in Rats Male, Upjohn Sprague Dawley rats were anesthetized with sodium pentobarbital and their dorsal hair removed with the depilatory NAIR. Care was taken to prevent abrasions which might result from hair removal. The animals were returned to their cages and allowed to recover for twenty-four hours. The rats were then fasted overnight in metal restraining tubes without water prior to treatment. 2-(4-ethylthio-3-methylpyridin-2-yl methyl)sulfinyl-benzimidazole at 0 or 100 mg/kg was applied to the backs of the rats and spread with an Eppendorf pipette tip. The same volume of DMSO alone was applied after 2 hrs to all animals. The rats were evaluated 5 or 30 hours after the initial dose for determination of $(H^+-K^+)$ ATPase activity.

Transdermal treatment with the subject compound reduced $(H^+-K^+)$ ATPase activity 60-65% from control. Activity did not change with time.

EXAMPLE 2

Effect of Transdermal Omeprazole in Rats

Male, Upjohn Sprague Dawley rats were anesthetized with sodium pentobarbital and their dorsal hair removed with the depilatory NAIR. Care was taken to prevent abrasions which might result from hair removal. The animals were returned to their cages and allowed to recover for twenty-four hours. The rats were then fasted overnight in metal restraining tubes without water prior to treatment. Omeprazole at 0 or 100 mg/kg was applied to the backs of the rats and spread with an Eppendorf pipette tip. The same volume of DMSO alone was applied after 2 hrs to all animals. The rats were evaluated 5 or 30 hours after the initial dose for determination of $(H^+-K^+)$ ATPase activity.

Transdermal treatment with omeprazole reduced $(H^+-K^+)$ ATPase activity 35% as compared to the control after 5 hours and 27% as compared to the control after 30 hours. Thus, demonstrating that the omeprazole was absorbed through the skin and inhibited $(H^+-K^+)$ ATPase activity.

EXAMPLE 3

Effect of Additional DMSO on Transdermal Activity

The rats were prepared as described in Example 1 and fasted overnight. The same compound as in Example 1 was applied at 0, 100 or 200 mg/kg. Additional volumes (100 $\mu$l) of DMSO were spread over the treatment area one time (after two hours) or four times (after one, two, three and four hours). The animals were evaluated 5 hours after the initial dose for determination of $(H^+-K^+)$ ATPase activity.

The transdermal treatment (100 mg/kg) reduced $(H^+-K^+)$ ATPase activity 65% from control. Additional applications of DMSO (four wipes) reduced the activity of the same dose an additional 16%. A 200 mg/kg dose with one wipe of DMSO after two hours reduced the $(H^+-K^+)$ ATPase activity by 72%. Thus, the additional applications of DMSO were more effective (81%) than a single application at twice the dosage (200 mg/kg).

EXAMPLE 4

Effect of Transdermal Applications in Rats: Dose Response

Rats were prepared as described in Example 1 and fasted overnight. The same compound as used in Example 1 was applied at 0, 25, 50, or 100 mg/kg. Additional volumes (100 μl) of DMSO were spread over the treatment area after 2, 5, and 7 hours. The animals were evaluated 24 hours after the initial dose for determination of $(H^+ \text{-} K^+)$ ATPase activity.

The results showed approximately a 50% reduction in $(H^+ \text{-} K^+)$ ATPase from the control indicating that the reduction in activity was at a maximum even at the lower dose. This suggests that a minimum of 4% of the lowest dose was absorbed.

EXAMPLE 5

Transdermal Activity in Rabbits

Male, New Zealand White rabbits were fasted overnight without water in their cages prior to treatment. The same compound as used in Example 1 was applied at 0 or 100 mg/kg in divided doses (½ to each ear) to naive rabbit ears. The rabbits received an additional application of DMSO to the treatment area after 1, 3, 5, 7, 24 and 25 hrs. The rabbits were evaluated 30 hrs after the initial dose for determination of $(H^+ \text{-} K^+)$ ATPase activity.

The results showed that the transdermal treatment reduced $(H^+ \text{-} K^+)$ ATPase activity 87% from control when applied to rabbit ears, no signs of irritation were observed.

The examples show that transdermal application of the subject compounds is effective for reducing $(H^+ \text{-} K^+)$ ATPase activity. Also, the effect remains long lasting when applied and no signs of irritation were apparent.

We claim:

1. A method for transdermally inhibiting the the secretion of gastric acid for prevention or treatment of gastrointestinal disease in mammals comprising: applying to the skin of a mammal a therapeutically effective amount of a compound of formula I

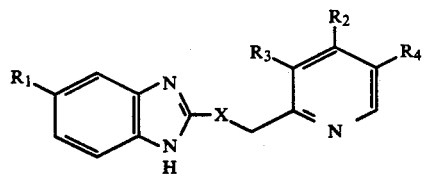

or a pharmaceutically acceptable salt thereof wherein
X is
  (a) =S, or
  (b) =S→O;
$R_1$ is
  (a) hydrogen,
  (b) methyl,
  (c) methoxy, or
  (d) trifluoromethyl;
$R_2$ is
  (a) methoxy,
  (b) —$SR_5$ wherein $R_5$ is ($C_1$-$C_4$)alkyl, ($C_1$-$C_4$)alkenyl, PhX, —$CH_2$PhX, or ($C_3$-$C_{10}$)cycloalkyl, wherein (PhX) is phenyl substituted by zero to 3 of the following: ($C_1$-$C_4$)alkyl, chloro, fluoro, bromo, nitro, trifluoromethyl, or $OR_3$; and
$R_3$ and $R_4$ are the same or different and are
  (a) hydrogen, or
  (b) ($C_1$-$C_4$)alkyl.

2. The method of claim 1 wherein said compound is first dissolved in a transdermal cream, paste, gel or liquid or otherwise absorbed into a transdermal patch.

3. The method of claim 1 wherein said compound is 2-(4-ethylthio-3-methylpyridin-2-yl methyl)sulfinyl-benzimidazole.

4. The method of claim wherein said compound is omeprazole, X is =S→O, $R_1$ and $R_2$ are methoxy and $R_3$ and $R_4$ are methyl.

5. The method of claim 2 wherein said compound is dissolved in an amount of from about 1 to about 300 mg/dose.

6. A pharmaceutical composition comprising: a compound of formula I

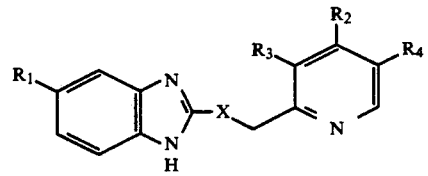

or a pharmaceutically acceptable salt thereof in a therapeutically effective amount; wherein
X is
  (a) =S, or
  (b) =S→O;
$R_1$ is
  (a) hydrogen,
  (b) methyl,
  (c) methoxy, or
  (d) trifluoromethyl;
$R_2$ is
  (a) methoxy
  (b) —$SR_5$ wherein $R_5$ is ($C_1$-$C_4$)alkyl, ($C_1$-$C_4$)alkenyl, PhX, —$CH_2$PhX, or ($C_3$-$C_{10}$)cycloalkyl, wherein (PhX) is phenyl substituted by zero to 3 to the following: ($C_1$-$C_4$)alkyl, chloro, fluoro, bromo, nitro, trifluoromethyl, or $OR_3$; and
$R_3$ and $R_4$ are the same or different and are
  (a) hydrogen, or
  (b) ($C_1$-$C_4$)alkyl; and a transdermal vehicle.

7. The pharmaceutical composition of claim 6 wherein said compound is 2-(4-ethylthio-3-methylpyridin-2-yl methyl)sulfinyl-benzimidazole.

8. The pharmaceutical composition of claim 6 wherein said compound is omeprazole, X is =S→O, $R_1$ and $R_2$ are methoxy and $R_3$ and $R_4$ are methyl.

9. The pharmaceutical composition of claim 6 wherein said transdermal vehicle is a cream, paste, gel or liquid or otherwise absorbed into a transdermal patch.

10. The pharmaceutical composition of claim 6 wherein said compound is dissolved in said transdermal vehicle in an amount of from about 1 to about 300 mg/dose.

* * * * *